United States Patent
Smith et al.

(10) Patent No.: US 11,078,433 B2
(45) Date of Patent: Aug. 3, 2021

(54) CONVERSION OF MIXTURES OF $C_2$–$C_8$ OLEFINS TO JET FUEL AND/OR DIESEL FUEL IN HIGH YIELD FROM BIO-BASED ALCOHOLS

(71) Applicant: Gevo, Inc., Englewood, CO (US)

(72) Inventors: Jonathan O. Smith, Highlands Ranch, CO (US); Madeline Sjodin, Denver, CO (US); Austin Vaillancourt, Denver, CO (US); Paul Starkey, Denver, CO (US); Steve Donen, Chanhassen, MN (US); Michelle Shebowich, Denver, CO (US)

(73) Assignee: GEVO, INC., Englewood, CO (US)

(*) Notice: Subject to any disclaimer, the term of this patent is extended or adjusted under 35 U.S.C. 154(b) by 0 days.

(21) Appl. No.: 16/383,251

(22) Filed: Apr. 12, 2019

(65) Prior Publication Data

US 2020/0010767 A1    Jan. 9, 2020

Related U.S. Application Data

(63) Continuation of application No. PCT/US2017/056793, filed on Oct. 16, 2017.
(Continued)

(51) Int. Cl.
C10G 50/00 (2006.01)
B01J 21/06 (2006.01)
(Continued)

(52) U.S. Cl.
CPC ............ *C10G 50/00* (2013.01); *B01J 21/066* (2013.01); *B01J 29/405* (2013.01); *B01J 29/65* (2013.01);
(Continued)

(58) Field of Classification Search
CPC .. C10G 50/00; C10G 3/00; C10G 2300/1088; C10G 2400/04; C10G 2400/08;
(Continued)

(56) References Cited

U.S. PATENT DOCUMENTS

| 4,388,177 A | 6/1983 | Bowes et al. |
| 4,698,452 A | 10/1987 | Le Van Mao et al. |

(Continued)

FOREIGN PATENT DOCUMENTS

| CN | 1379005 A | 11/2002 |
| EP | 2374781 | 10/2011 |

(Continued)

OTHER PUBLICATIONS

Fan, et al., "Ethylene Formation by Catalytic Dehydration of Ethanol with Industrial Considerations", Materials (2013); 6(1): 101-115. Epub Dec. 28, 2012.
(Continued)

*Primary Examiner* — Ali Z Fadhel
(74) *Attorney, Agent, or Firm* — Cooley, LLP (57) ABSTRACT

The present disclosure provides methods and materials for oligomerization of lower olefins (e.g., $C_2$-$C_8$) to transportations fuels including diesel and/or jet fuel. The oligomerization employs, in certain embodiments, tungstated zirconium catalysts. Surprisingly, the oligomerizations proceed smoothly in high yields and exhibit little to no sensitivity to the presence of significant amounts of oxygenates (e.g., water, lower alcohols such as $C_2$-$C_8$ alcohols) in the feed stream. Accordingly, the present disclosure is uniquely suited to the production of fuels derived from bio-based alcohols, wherein olefins produced from such bio-based alcohols typically contain high levels of oxygenates.

38 Claims, 2 Drawing Sheets

Related U.S. Application Data (60) Provisional application No. 62/539,287, filed on Jul. 31, 2017, provisional application No. 62/521,664, filed on Jun. 19, 2017, provisional application No. 62/500,892, filed on May 3, 2017, provisional application No. 62/489,756, filed on Apr. 25, 2017, provisional application No. 62/484,580, filed on Apr. 12, 2017, provisional application No. 62/426,787, filed on Nov. 28, 2016, provisional application No. 62/412,046, filed on Oct. 24, 2016, provisional application No. 62/408,476, filed on Oct. 14, 2016.

(51) Int. Cl.
| | |
|---|---|
| *B01J 29/40* | (2006.01) |
| *B01J 29/65* | (2006.01) |
| *C07C 2/08* | (2006.01) |
| *C07C 2/04* | (2006.01) |
| *C07C 2/06* | (2006.01) |
| *C07C 2/10* | (2006.01) |
| *C07C 2/02* | (2006.01) |

(52) U.S. Cl.
CPC ............... *C07C 2/04* (2013.01); *C07C 2/06* (2013.01); *C07C 2/08* (2013.01); *C07C 2/10* (2013.01); *C07C 2/02* (2013.01); *C10G 2300/1088* (2013.01); *C10G 2400/04* (2013.01); *C10G 2400/08* (2013.01)

(58) Field of Classification Search
CPC ..... C10G 2300/1092; C07C 2/08; C07C 2/04; C07C 2/06; C07C 2/10; C07C 2/02; C07C 2521/06; C07C 2523/28; C07C 2523/30; C07C 2523/75; C07C 2523/755; C07C 2523/882; C07C 2523/883; C07C 2523/888; C07C 2529/40; C07C 2529/65; C07C 2/12; C07C 1/24; C07C 1/20; B01J 21/066; B01J 29/405; B01J 29/65; Y02P 30/20; Y02P 20/52; C08G 1/02; C10C 1/20

See application file for complete search history.

(56) References Cited

U.S. PATENT DOCUMENTS

| | | | |
|---|---|---|---|
| 5,113,034 A | 5/1992 | Soled et al. | |
| 5,608,133 A | 3/1997 | Chang et al. | |
| 5,639,798 A | 6/1997 | Wilson et al. | |
| 6,914,165 B2 | 7/2005 | Flego et al. | |
| 9,593,054 B2* | 3/2017 | Kania | C10G 3/46 |
| 9,688,590 B2 | 6/2017 | Cross, Jr. et al. | |
| 2003/0105171 A1 | 6/2003 | Subramanian et al. | |
| 2004/0015028 A1* | 1/2004 | Brown | C07C 2/12 |
| | | | 585/520 |
| 2004/0138051 A1* | 7/2004 | Shan | B01J 23/26 |
| | | | 502/60 |
| 2005/0011911 A1 | 1/2005 | Vaughan | |
| 2005/0100494 A1 | 5/2005 | Yaluris et al. | |
| 2006/0052236 A1* | 3/2006 | Angevine | B01J 35/1057 |
| | | | 502/66 |
| 2009/0182183 A1 | 7/2009 | Keenan et al. | |
| 2010/0168487 A1 | 7/2010 | Sawyer et al. | |
| 2010/0216958 A1 | 8/2010 | Peters et al. | |
| 2011/0288352 A1* | 11/2011 | Peters | C10G 3/44 |
| | | | 585/14 |
| 2012/0142984 A1* | 6/2012 | Roberts | C10G 3/45 |
| | | | 585/275 |
| 2012/0198760 A1* | 8/2012 | Blommel | C10G 3/48 |
| | | | 44/437 |
| 2012/0238787 A1* | 9/2012 | Gruber | C10G 3/00 |
| | | | 585/14 |
| 2012/0283499 A1* | 11/2012 | Nesterenko | C10G 50/00 |
| | | | 585/520 |
| 2013/0131411 A1 | 5/2013 | Blommel et al. | |
| 2013/0245348 A1 | 9/2013 | Vermeiren et al. | |
| 2013/0338414 A1* | 12/2013 | Fingland | C10G 45/62 |
| | | | 585/310 |
| 2014/0065059 A1 | 3/2014 | Suzuki et al. | |
| 2014/0114101 A1 | 4/2014 | Greene et al. | |
| 2017/0050896 A1 | 2/2017 | Yasukawa et al. | |

FOREIGN PATENT DOCUMENTS

| | | |
|---|---|---|
| JP | 2005/015383 A | 1/2005 |
| JP | 2005/015384 A | 1/2005 |
| WO | WO 2002/004575 A2 | 1/2002 |
| WO | WO 2018/071905 A1 | 4/2018 |

OTHER PUBLICATIONS

Hauge, et al., "Oligomerization of isobutene over solid acid catalysts", Catalysis Today (2005); 100(3-4): 463-466.

International Preliminary Report on Patentability for International Application No. PCT/US2017/056793, dated Apr. 16, 2019, 10 pages.

International Search Report and Written Opinion for International Application No. PCT/US2017/056793, dated Jan. 2, 2018, 12 pages.

Lee, et al., "Trimerization of isobutene over $WO_x/ZrO_2$ catalysts", Applied Catalysis A: General (2009); 366(2): 299-303.

Mantilla, et al., "Catalytic behavior of sulfated $TiO_2$ in light olefins oligomerization", J. Molecular Catalysis A (2005); 228(1-2): 333-338.

Mathew, et al., "Influence of nature of support on the catalytic activity of supported molybdenum-oxo species in benzyl alcohol conversion", Journal of Molecular Catalysis A: Chemical (2006); 255(1-2): 243-248.

Mérida-Robles, et al., "Characterization of Ni, Mo and Ni—Mo catalysts supported on alumina-pillared a-zirconium phosphate and reactivity for the thiophene HDS reaction", Journal of Molecular Catalysis A: Chemical (1999); 145(1-2): 169-181.

Ramesh, et al., "Structure and reactivity of phosphorous modified H-ZSM-5 catalysts for ethanol dehydration", Catalysis Communications (Jan. 25, 2009); 10(5): 567-571.

Van Schalkwyk, et al., "Factors that could influence the activity of a WO3/SiO2 catalyst: Part III", Applied Catalysis A: General (2003); 255(2): 143-152.

Vosmerikov, et al., "Conversion of the straight-run gasoline fraction of high-paraffin oil on a zeolite catalyst", Petroleum Chemistry (2011); 51(2): 143-149.

Extended European Search Report in European Patent Application No. 17860581.2 dated May 18, 2020, 10 pages.

Fehér, et al., "Oligomerisation of isobutene with silica supported ionic liquid catalysts". Green Chem. (2012); 14(2): 403-409. First Published Dec. 23, 2011.

Heveling, et al., "Oligomerization of ethene over nickel-exchanged zeolite y into a diesel-range product". Applied Catalysis (Sep. 15, 1988); 42(2): 325-336.

Muraza, Oku, "Maximizing Diesel Production through Oligomerization: A Landmark Opportunity for Zeolite Research". Ind. Eng. Chem. Res. (2015); 54(3): 781-789. Publication Date: Dec. 31, 2014.

Venuto and Landis, "Organic Catalysis over Crystalline Aluminosilicates". Advances in Catalysis (1968); 18: 259-371, 149 pages.

* cited by examiner

CONVERSION OF MIXTURES OF $C_2$—$C_8$ OLEFINS TO JET FUEL AND/OR DIESEL FUEL IN HIGH YIELD FROM BIO-BASED ALCOHOLS

PRIORITY INFORMATION

This application is a continuation of and claims the priority benefit, under 35 U.S.C. 111(a), of International Application Serial No. PCT/US17/056793, filed Oct 16, 2017, entitled "CONVERSION OF MIXTURES OF C2-C8 OLEFINS TO JET FUEL AND/OR DIESEL FUEL IN HIGH YIELD FROM BIO-BASED ALCOHOLS," which claims the benefit of U.S. Provisional Application Nos. 62/408,476, filed on Oct. 14, 2016; 62/412,046, filed on Oct. 24, 2016; 62/426,787, filed on Nov. 28, 2016; 62/484,580, filed on Apr. 12, 2017; 62/489,756, filed on Apr. 25, 2017; 62/500,892, filed on May 3, 2017; 62/521,664, filed on Jun. 19, 2017, and 62/539,287, filed on Jul. 31, 2017; each of which is incorporated herein by reference in its entirety.

TECHNICAL FIELD

This disclosure relates to a process for converting lower linear and branched mono-olefins derived from $C_2$-$C_5$ bio-based alcohols to higher hydrocarbons, which are useful as precursors towards Jet or Diesel fuel production. In certain embodiments, Gevo researchers have developed technology converting bio-based $C_2$-$C_5$ alcohols to their respective linear and branched olefins in high yield, followed by subsequent oligomerization of branched and/or linear $C_2$-$C_8$ olefins to renewable Jet Fuel and/or Diesel fuel in overall yields of at least 70% in the presence of tungstated zirconium catalysts, nickel and/or cobalt doped tungstated zirconium catalysts, zeolites, or metal (Group IB-VIIB) doped zeolites and/or catalyst combinations thereof.

BACKGROUND

Bioethanol is a significant commodity chemical product. With the increased availability and reduced cost of bioethanol, researchers have explored bioethanol as a feedstock for making a variety of downstream hydrocarbons, including the aforementioned Jet Fuel and/or Diesel Fuel. Additionally, Gevo researchers have developed a fermentative process facilitating bio-isobutanol production, thereby providing a new route to bio-based fuels based on mixtures of bio-based alcohols.

Dehydration of $C_2$-$C_5$ alcohols and in some cases their subsequent isomerization is documented in the literature (*Materials* 2013,6,101-115; *Catalysis Communications* 10, 2009, 567-571; US 20130131411; US 2017/0050896; EP 2374781), but few reports target catalysts aimed at dehydrating mixtures of bio-based $C_2$-$C_5$ alcohols directly followed by oligomerization to hydrocarbon Jet and/or Diesel fuel in a fully integrated mode.

The oligomerization of gaseous mono-olefins so as to form gasoline-type hydrocarbons is known, and has been disclosed in the patent literature (U.S. Pat. Nos. 4,613,719; 9,688,590). However, there is an ever present need to develop new oligomerization processes employing more effective and/or less expensive catalyst compositions.

The oligomerization reaction of olefins has been carried out by using acid catalysts such as supported phosphoric acid, and olefin dimers have been generally obtained for gasoline additive after hydrogenation of the dimers (U.S. Pat. Nos. 6,689,927, 6,284,938).

Recently, several oligomerization methods to prepare trimers are reported. Olefin trimerization has been mainly carried out by using solid acid catalysts such as heteropoly acid (JP 2005015383), zirconia (JP 2005015384), zeolite called A1-TS-I (U.S. Pat. No. 6,914,165) and sulfated titania (J. Molecular Catalysis A, 228, 333, 2005). Ionic liquids are also used for the reaction (CN 1379005).

Additionally, numerous examples have been reported that utilize cation exchange resins for the oligomerization. It has been claimed that a cation exchange resin can be used in a dimerization (USP 2005/011911 IA1). U.S. Pat. No. 5,789,643 taught that oligomerization could be catalyzed by zeolites, aluminas and ion exchange resins. Tetramers or pentamers could be obtained by the oligomerization of pre-formed dimers with ion exchange resins (U.S. Pat. No. 6,239,321).

Moreover, an ion exchange resin called Amberlyst-15 was used in the oligomerization of isobutene (Catalysis Today, 100, 463, 2005). However, the conversion was less than 40%, and dimers rather than trimers were the main products. Similarly, Amberlyst-35 ion exchange resin affords higher levels of trimers, but dimers are present in 30-40% levels.

Additionally, nickel based heterogeneous catalysts are routinely used for ethylene oligomerization in order to provide mixtures of $C_2$-$C_8$ olefins which are secondarily oligomerized to $C_8$-$C_{20}$ olefins (U.S. Pat. Nos. 2,381,198, 2,581,228, 3,527,839).

Most industrial processes produce oligomers in a non-selective manner by the oligomerization of $C_2$-$C_6$ olefins. Such processes typically generate a mathematical distribution (Schulz-Flory or Poisson) of oligomers, which very often does not match market demand.

SUMMARY OF THE INVENTION

This disclosure relates to a process for converting lower linear and branched mono-olefins derived from $C_2$-$C_5$ bio-based alcohols to higher hydrocarbons, which are useful as precursors towards Jet or Diesel fuel production. In certain embodiments, a process for converting one or more $C_2$-$C_8$ linear or branched olefins to jet and/or diesel fuel, including contacting a feed stream comprising the one or more $C_2$-$C_8$ linear or branched olefins with a first catalyst to afford a mixture comprising at least 70 wt % $C_{12}$ or greater alkenes is described.

In some embodiments, the one or more $C_2$-$C_8$ linear or branched olefins comprise at least about 50 wt % of butenes, at least about 75 wt % of butenes, and at least about 90 wt % of butenes. Said butenes may comprise at least about 75 wt % isobutene or 75 wt % of linear butenes.

The process can further comprise dehydrating one or more $C_2$-$C_8$ linear or branched alcohols to provide the feed stream comprising one or more $C_2$-$C_8$ linear or branched olefins. The feed stream comprising one or more $C_2$-$C_8$ linear or branched olefins includes at least 0.5 wt % oxygenates, at least 1 wt % oxygenates, at least 2 wt % oxygenates, and at least 3 wt % oxygenates. The oxygenates can comprise water and one or more $C_2$-$C_8$ linear or branched alcohols. The yield of said $C_{12}$ or greater alkenes can be at least about 50%, at least about 60%, at least about 70%, and at least about 75%.

In some embodiments, the first catalyst comprises tungstated zirconium catalysts, molybdenum zirconium catalysts, nickel and/or cobalt doped tungstated zirconium catalysts, nickel and/or cobalt doped molybdenum zirconium catalysts, zeolites, Group IB-VIIB metal doped zeolites) doped zeolites, or combinations thereof. The tungstated zirconium catalyst can comprise about 85 wt % zirconium and about 15 wt % tungsten. The tungstated zirconium catalyst can further comprise from about 0.01 to about 3 wt % of nickel. The tungstated zirconium catalyst can further comprises from about 0.01 to about 3 wt % of cobalt. The molybdenum zirconium catalyst can comprise about 85 wt % zirconium and about 15 wt % molybdenum. The molybdenum zirconium catalyst can further comprise from about 0.01 to about 3 wt % of nickel. The molybdenum zirconium catalyst can further comprise from about 0.01 to about 3 wt % of cobalt. The first catalyst can comprise an acidic zeolite catalyst. The first catalyst can comprise an acidic ZSM-5 catalyst. The acidic ZSM-5 can further comprise from about 0.01 wt % to about 5 wt % zinc. The acidic ZSM-5 can further comprise from about 0.01 wt % to about 20 wt % zirconium. The first catalyst can comprise an acidic Ferrierite catalyst. The acidic Ferrierite can further comprise from about 0.01 wt % to about 5 wt % zinc. The acidic Ferrierite can further comprise from about 0.01 wt % to about 20 wt % zirconium.

In some embodiments, the second catalyst comprises Zeolites, Group IB-VIIB metal doped zeolites) doped zeolites, or combinations thereof. The second catalyst can comprise an acidic ZSM-5 catalyst. The acidic ZSM-5 can further comprise from about 0.01 wt % to about 5 wt % zinc. The acidic ZSM-5 can further comprise from about 0.01 wt % to about 20 wt % zirconium. The second catalyst can comprise acidic Ferrierite catalyst. The acidic Ferrierite can further comprise from about 0.01 wt % to about 5 wt % zinc. The acidic Ferrierite further comprises from about 0.01 wt % to about 20 wt % zirconium.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

DETAILED DESCRIPTION

In the following description, certain specific details are set forth in order to provide a thorough understanding of various embodiments. However, one skilled in the art will understand that the disclosure may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed disclosure.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The word 'about' when immediately preceding a numerical value means a range of plus or minus 10% of that value, e.g., "about 50" means 45 to 55, "about 25,000" means 22,500 to 27,500, etc. Furthermore, the phrases "less than about" a value or "greater than about" a value should be understood in view of the definition of the term "about" provided herein.

The present inventors have made intensive research to overcome the shortcomings described above, and as a result, have developed novel oligomerization processes in which a tungstated (or molybdenum doped) zirconium, nickel or cobalt doped tungstated zirconium, zeolite or metal doped zeolite, and/or combinations of catalysts are used in the reaction resulting in mixed olefin conversions to either Jet fuel or Diesel fuel hydrocarbons in yields exceeding 60%. Accordingly, the object of this invention is to provide a process for producing olefinic $C_{12}$+ oligomers in high selectivity, high throughput, and long catalyst life that meet or exceed Jet and/or Diesel fuel specifications. Those skilled in the art will recognize that in order to meet Jet fuel and/or Diesel fuel specifications the appropriate balance of branched and/or linear oligomers is desirable in the oligomerization feedstock, and as such catalysts that concurrently isomerize and/or oligomerize mixtures of branched and/or linear $C_2$-$C_8$ olefins in high yield and conversion are desired. In certain embodiments, depending on the bio-based alcohol ($C_2$-$C_5$) feedstock mixture introduced, catalysts that additionally facilitate isomerization and/or structural rearrangement during the dehydration step are desirable in order to produce the $C_2$-$C_8$ olefinic feedstock for oligomerization. The ability to selectively oligomerize branched olefins, in the presence of linear olefins, increases process flexibility towards either Jet and/or Diesel fuel production depending on market fluctuations.

The present invention is directed to novel processes for i) preparing a mixture of branched and/or linear $C_2$-$C_8$ olefins via novel dehydration catalysts, and ii) preparing $C_{12}$+ olefins via oligomerizing mixtures of linear and/or branched C2-C8 olefins, wherein tungstated zirconium, nickel or cobalt doped tungstated zirconium, zeolite or metal doped zeolite, and/or combinations of catalysts are used as catalysts. The present invention will be described in more detail as follows:

The olefins described in this invention are any olefins composed of $C_2$ or higher carbon, preferentially to be branched and/or linear $C_2$-$C_8$ mixtures of unsaturated hydrocarbons, and more preferentially to be mixtures of ethylene ($C_2H_4$), propylene ($C_3H_6$), butylenes ($C_4H_8$), pentenes ($C_5H_{10}$), and hexenes ($C_6H_{12}$) as the most suitable olefins.

The preferential dehydration temperature of mixtures of branched and/or linear $C_2$-$C_5$ alcohols is from 250° C. to 400° C., with reaction pressures ranging from 0-100 psig.

The dehydration reaction is performed in continuous mode for mass production of olefins. The continuous mode is operated by using a fixed bed reactor, and reactant flows can be upward or downward.

The preferential oligomerization temperature is from 100° C. to 300° C. (e.g., about 100° C., about 110° C., about 120° C., about 130° C., about 140° C., about 150° C., about 160° C., about 170° C., about 180° C., about 190° C., about 200° C., about 210° C., about 220° C., about 230° C., about 240° C., about 250° C., about 260° C., about 270° C., about 280° C., about 290° C., about 300° C.), with reaction pressures ranging from 200-600 psig (e.g., about 220 psig, about 240 psig, about 260 psig, about 280 psig, about 300 psig, about 320 psig, about 340 psig, about 360 psig, about 380 psig, about 400 psig, about 420 psig, about 440 psig, about 460 psig, about 480 psig, about 500 psig, about 520 psig, about 540 psig, about 560 psig, about 580 psig, about 600 psig).

The oligomerization reaction is performed in continuous mode for mass production of oligomers. The continuous mode is operated by using a fixed bed reactor, and reactant flows can be upward or downward. It is advisable to use a recycle stream consisting of oligomerized reaction product to control the heat of reaction, as the oligomerization reaction is very exothermic.

Granular or extruded catalysts are suitable for the reaction even though no specific size and morphology are mandatory. Catalyst with size greater than 0.1 mm is more suitable, and the size of 0.2-1.0 mm is most suitable for the operation ability and low pressure drop.

$C_2$-$C_5$ alcohol conversion through dehydration is typically higher than about 90% (e.g., about 91%, about 92%, about 93%, about 94%, about 95%, about 96%, about 97%, about 98%, about 99. Typical olefin conversion is higher than about 60% (e.g., about 65%, about 70%, about 75%, about 80%, about 85%, about 90%). In some embodiment, the conversion is higher than about 90%, because selectivity to olefin trimers increases with increasing olefin conversion. If olefin conversion is too low, the formation of lower molecular weight oligomers, such as olefin dimers cannot be avoided, whereas olefin tetramers can be increased slightly when the olefin conversion is too high.

Productivity is low, and the concentration of high molecular weight oligomers is high when the flow rate or space velocity of reactant is too low. On the other hand, the olefin conversion and trimers selectivity are low if the space velocity is too high. The suitable space velocity, based on the olefin WHSV (weight hourly space velocity), is 2-100 $h^{-1}$, and more preferably the velocity is 5-20 $h^{-1}$.

The trimers and tetramers obtained from the olefin oligomerization can be utilized directly for the production of Jet and Diesel fuel post hydrogenation. Hydrogenation catalysts can be selected from any supported catalysts such as Pd/C, Pd/alumina, Pd/silica, Pd/silica-alumina, Pt/C, Pt/alumina, Pt/silica, Pt/silica-alumina, Ru/C, Ru/alumina, Ru/silica, Ru/ silica-alumina, Ni/C, Ni/alumina, Ni/silica, Ni/silica-alumina.

Efforts aimed at making Renewable Jet in high yields from mixtures of bio-based ethylene, propylene, and/or butylenes identified a selective oligomerization process resulting in mass yields to Jet Fuel and/or Diesel fuel exceeding at least 70%. Surprisingly, the oligomerization process can be operated at relatively low temperatures and pressures with $WO_x/ZrO_y$ catalysts, or $Mo_xZrO_y$ catalysts with 15 wt % W or Mo loading on $ZrO_y$ support, which are relatively inexpensive and commercially available catalysts.

Specifically, the oligomerization of liquefied linear $C_2$-$C_8$ olefins with $WO_x/ZrO_y$ catalyst proceeds smoothly at reaction pressures of 250-600 psig, reaction temperatures of 125-350° C., and a liquid hourly space velocity (LHSV) of 1.5-2.5 resulting in a single pass $C_2$-$C_8$ olefin conversion of at least 70% with a product oligomer distribution of 1% $C_4$, 18% $C_8$, 65% $C_{12}$, 14% $C_{16}$, and 1.5% $C_{20}$, as exemplified in the examples below. Removal and recycle of the 'light' $C_2$-$C_8$ oligomer fraction provides an overall isolated Jet yield of at least 70% based on olefins fed. The $WO_x/ZrO_y$ catalysts are stable, and extended reaction on-stream times have been demonstrated both in the lab and at demo plant scale. In addition, the $WO_x/ZrO_y$ catalyst can be regenerated via air to regain activity.

Previous work (Lee et al, Applied Catalysis A: General, 366, 2009, 299-303) utilizing these $WO_x/ZrO_y$ catalyst were aimed at oligomerizing isobuylene to a mixture of $C_{12}$ and $C_{16}$ olefins utilizing n-butane as a diluent (50:50, isobutylene:n-butane). However, this is the first report using a similar catalyst for the production of Jet or Diesel fuel, via linear $C_2$-$C_8$ olefin oligomerization with or without the presence of isobutylene, and with no diluent present.

The $C_2$-$C_8$ Olefin Oligomerization process with $WO_x/ZrO_y$ catalysts results in high yield and selectivity to bio-based Jet or Diesel fuel at relatively low temperatures and pressures, and tolerate high levels of oxygenates. Other known catalysts for $C_2$-$C_8$ linear Olefin oligomerization (Zeolites, modified Zeolites, SPA's, Nafion Resins, etc) deactivate rapidly requiring re-activation, are relatively expensive, have poor tolerance for the presence of oxygenates, and result in higher levels of oligomer cracking/isomerization as evidenced by higher levels of $C_{5-7}$ dimers and lesser amounts of isolated yields to Jet and/or Diesel fractions.

Likewise, the isobutylene oligomerization process utilizing $WO_x/ZrO_y$ (10 wt % W) catalysts results in high yield and selectivity to bio-based Jet fuel at relatively low temperatures and pressures. Surprisingly, the $WO_x/ZrO_y$ (10 wt % W) catalyst results in an extremely 'clean' oligomer distribution with high single-pass yield to Jet Fuel, as exemplified by the 'water' clear olefinic product, as compared to a 'yellowish' colored oligomerization product when utilizing other known oligomerization catalysts.

The $WO_x/ZrO_y$ (10 wt % W) catalyst is an improvement over the previously reported $WO_x/ZrO_y$ catalyst with 15 wt % W loading (Lee et al, Applied Catalysis A: General, 366, 2009, 299-303), as exemplified by a 'cleaner' olefinic product, and higher single-pass yield to Jet in comparison. Another surprising feature of the $WO_x/ZrO_y$ (10 wt % W) catalyst is the isomeric purity of the $C_8$ olefinic 'light' fraction, which consists of at least 90% to the preferred 2,4,4-trimethylpentene isomer with <10% of the undesirable 2,3,4-trimethylpentene. The 2,4,4-trimethylpentene is i) the $C_8$ olefinic isomer required for formation of p-Xylene in high selectivity via dehydrocyclization reaction, ii) is the precursor to the pure high octane 2,2,4-trimethylpentane compound, and iii) most easily dimerizes to the $C_{16}$ olefin which is necessary for producing other grades of Jet Fuel (eg JP5).

Dehydration of biobased $C_2$-$C_6$ alcohols results in significant levels of $C_2$-$C_8$ linear plus branched $C_4$-$C_8$ olefins, aromatics, and with minor amounts of paraffins depending upon catalysts employed. In certain embodiments, Gevo researchers have identified metal doped Zeolite catalysts that result in i) significant levels of isomerization to $C_4$ linear olefins from $C_4$ branched alcohols with minimal amounts of aromatics and $C_5$+ olefins, ii) significant levels of isomerization to $C_4$ linear olefins from $C_4$ branched alcohols along with significant levels of aromatics and $C_5$+ olefins, iii) improved on-stream stability, iv) complete dehydration of ethanol to ethylene at a relatively low reaction temperature of 300° C., and v) catalyst regeneration via air.

Catalyst preparations are accomplished via impregnation or co-precipitation techniques depending upon selectivity desired and/or feedstock compositions. The ability to control the level of skeletal isomerization along with the amount of aromatics and $C_5$+ olefins across the dehydration step maximizes process flexibility and plant economics.

The subsequent oligomerization of these 'crude' olefinic streams, without purification to remove oxygenates and/or water, results in formation of Diesel, Jet, and/or Gasoline fractions in high yields via a $WO_x/ZrO_y$ (15 wt % W or 15 wt % Mo) catalyst impregnated with Nickel and/or Cobalt, or combinations incorporating type IB-VIIB metals. Additionally, a physical mixture of the impregnated $WO_x/ZrO_y$ catalyst with type H+ZSM-5 Zeolite catalyst provides additional benefits with regard to maximizing both conversion and extent of reaction of the olefinic mixtures to a $C_{12}$+ fraction. As required, the impregnated $WO_x/ZrO_y$ catalyst, and nickel or cobalt impregnated $WO_x/ZrO_y$ catalyst physically mixed with a H+ZSM-5 Zeolite catalyst, or a H+ZSM-5 Zeolite catalyst can be regenerated via air to regain activity.

Gevo has developed catalytic technology that converts bio-based isobutanol and/or ethanol to isobutylene or propylene in high yields with significant levels of linear and branched $C_2$-$C_6$ olefins. The isobutylene containing $C_2$-$C_6$ linear and branched olefins can subsequently be oligomerized utilizing these novel $WO_x/ZrO_y$ based catalysts and/or catalyst combinations to renewable Diesel ($C_{12}$+ fraction), Jet fuel ($C_{12}$+ fraction) or Gasoline ($C_8$'s) fuel in overall yields of at least 70%, and more preferably 90%, depending upon temperature, pressure, and flow rates (eg WHSV). One skilled in the art will immediately recognize the applicability of this catalyst and oligomerization technology for converting 'crude' un-deoxygenated petro-based refinery streams containing mixtures of $C_2$-$C_8$ olefins to higher value liquid fuel fractions in a single step.

Figure 1:
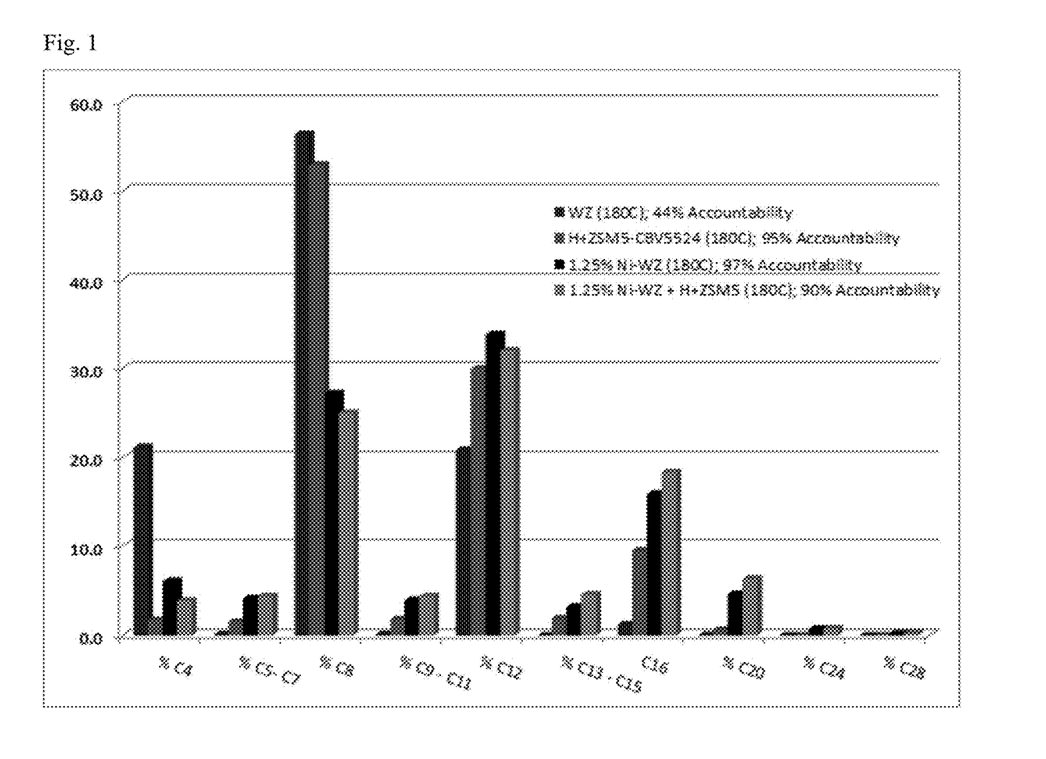
FIG. 1 shows oligomerization of mixed C4 Olefin Feed (16.5% n-Butene, 16.5% cis-Butene, 16.5% trans-Butene, 50.5% Isobutylene) over Tungstated Zirconium doped with 1.23% Nickel (T=180° C., P=345 psig, WHSV=1.8), Tungstated Zirconium without Ni, H$^+$ZSM-5, and Tungstated Zirconium doped with 1.23% Nickel in combination with H$^+$ZSM-5.
Figure 2:
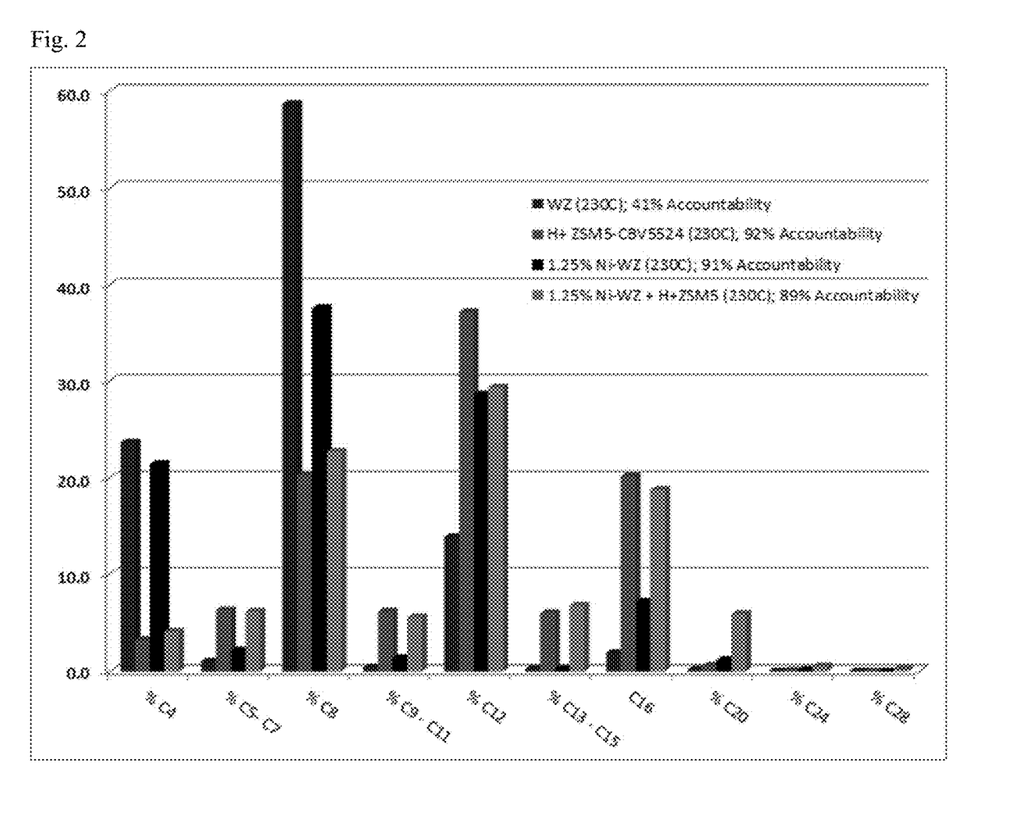
FIG. 2 shows oligomerization of mixed C4 Olefin Feed (16.5% n-Butene, 16.5% cis-Butene, 16.5% trans-Butene, 50.5% Isobutylene) over Tungstated Zirconium doped with 1.23% Nickel (T=230° C., P=345 psig, WHSV=1.8), Tungstated Zirconium without Ni, H$^+$ZSM-5, and Tungstated Zirconium doped with 1.23% Nickel in combination with H$^+$ZSM-5.

Data in FIGS. 1 and 2 below exemplifies the surprising impact on linear olefin conversion and mass accountability, via doping tungstated zirconium catalyst with Cobalt and/or Nickel, in combination with H+ZSM-5 Zeolites at 180° C. and 230° C. (FIGS. 1-2), versus the un-doped tungstated zirconium catalyst and versus H+ZSM-5 by itself.

In accordance with the invention, there is provided a process for producing Diesel, Jet and/or Gasoline fractions from predominately olefinic compounds, preferably having a Cetane number of 35 or above, a research octane number (RON) of 80 or above, meeting Jet Fuel specifications, and having therein no more than about 1-5% by weight of aromatics. Said process comprising contacting $C_2$-$C_8$ olefins with a H+ZSM-5 type Zeolite, at a WHSV of from about 0.1 to about 25 and at a temperature of from about 80° C. to about 350° C., whereby said Diesel, Jet, or Gasoline fractions containing predominantly higher olefins is obtained. Data in FIGS. 1 and 2 below exemplifies the surprising impact on linear and branched olefin conversion, and mass accountability utilizing the H+ZSM-5 catalyst.

Efforts aimed at making Renewable Jet in high yields from bio-based isobutanol and/or ethanol identified a selective oligomerization process resulting in exemplary mass yields to Diesel Fuel exceeding at least 70%. Surprisingly, the oligomerization process can be operated at relatively low temperatures and pressures with Nickel or Cobalt impregnated $WO_x/ZrO_y$ catalysts containing 15 wt % W loading on $ZrO_y$ support, which are relatively inexpensive and commercially available catalysts from Clariant and others. Specifically, the oligomerization of liquefied isobutylene with 0.05-5 wt % Cobalt and/or Nickel on $WO_x/ZrO_y$ catalyst proceeds smoothly at reaction pressures of 250-600 psig, reaction temperatures of 170-350° C., and a liquid hourly space velocity (LHSV) of 1.5-2.5 resulting in a single pass olefin conversion of at least 70% with a 'typical' oligomer distribution reflective of significant levels of isomerization and rearrangement as depicted by the Diesel Fuel distillation profile, versus Jet Fuel distillation profiles shown in FIG. 1. Removal and recycle of the $C_4$-$C_8$ oligomer fraction results in overall isolated Diesel yields of at least 70% based on olefins fed. Alternatively, the 'lights' $C_4$-$C_8$ oligomer fraction could be removed, via distillation, and marketed as high octane gasoline due to level of branched and linear olefins as a result of isomerization and rearrangement during oligomerization. The Cobalt and/or Nickel impregnated $WO_x/ZrO_y$ catalysts are stable and extended reaction on-stream times have been demonstrated. In addition, the Cobalt and/or Nickel impregnated $WO_x/ZrO_y$ catalyst can be regenerated via air to regain activity.

Oligomerization of crude renewable butylenes containing high levels of water, alcohols, and oxygenates to Jet Fuel proceeds smoothly over 15 wt % tungstated zirconium catalyst. The Capex and Variable cost of a commercial Jet Unit is significantly reduced by not requiring purification of the 'crude' olefin stream, obtained from the dehydration of renewable isobutanol, prior to oligomerization. Typically, so-called 'modifiers,' including of alcohols, water, and oxygenates, are purposely added to the feed of the oligomerization unit to reduce catalytic activity therein, enabling selective formation of high levels of $C_8$ olefins in proportion to $C_{12}$ and larger oligomers. As such, the addition of modifiers, typically results in unacceptably low yields to Jet Fuel ($C_{12}$ and higher olefins) with a corresponding high yield to $C_8$ olefins.

Surprisingly, we have found the presence of high levels of alcohol, water, and oxygenates, which would be expected to result in commercially unacceptable low yields, does not result in catalyst deactivation of a tungstated zirconium catalyst, and yields to Jet Fuel ($C_{12}$+ oligomers) of at least 75% can be maintained without pre-purification of an isobutylene feed to an oligomerization unit. Moreover, near complete single-pass isobutylene conversion can be effected.

Additionally, by adjusting the weight hourly space velocity (WHSV), in conjunction with adjustment of the recycle ratio of the oligomerization reactor effluent, an on-stream 80% yield of Jet Fuel can be sustained while simultaneously "tuning" or adjusting the $C_{12}/C_{16}/C_{20}$ oligomer ratios required to meet Jet fuel specifications (e.g., Jet A, Jet A-1, JP-5, JP-9, etc.) with regard to boiling point and viscosity. Operating outside optimal WHSV and recycle ratios can be problematic. For example, operating at too high a WHSV, with too low a recycle ratio, results in over oligomerization as observed by unacceptably high levels of $C_{16}$ and larger oligomers relative to the $C_{12}$ oligomers in a product stream. These higher levels of $C_{16}$ and larger oligomers result in a higher viscosity product that does not meet typical Jet Fuel specification viscosity requirements, and necessitates an additional separation step (e.g., vacuum distillation) to remove a portion of the $C_{16}$ oligomers, thus resulting in lower overall yields to Jet Fuel.

Additionally, we were surprised to learn that by tuning the WHSV of the fresh feed of 'crude' isobutylene in relation to the reactor effluent recycle ratio, the $C_{12}/C_{16}/C_{20}$ oligomer ratio can be 'fixed' (e.g., held relatively constant), while still being able to control the extent of the oligomerization process to increase Jet Fuel yield to at least 75%. Furthermore, adjusting oligomerization reaction temperature lower in conjunction with adjustments in WHSV had a minimal impact on the oligomer distribution exemplifying robustness of the $WO_x/ZrO_y$ catalyst. Another unexpected finding of the present oligomerization process is that the isomeric purity of co-produced 2,4,4-trimethylpentenes ($C_8$ olefins) in ~15-20% yield exceeds 90% selectivity of all C8 oligomers produced, while still maintaining at least 75% yield of Jet fuel. Typically, in order to increase the extent of oligomerization to maximize isobutylene conversion and concomitantly maximize yield of Jet Fuel, higher temperatures and more active catalysts are generally needed, resulting in higher levels (~35-40%) of isomerized 2,3,4-trimethylpentene. Isomeric purities of >90% for 2,4,4-trimethylpentene is necessary to obtain high octane, renewable iso-octane.

Moreover, high isomeric purity of 2,4,4-trimethylpentene formation can afford high isomeric purity renewable p-xylene via dehydrocyclization of the 2,4,4-trimethylpentene isomer. Table 3 below provides yield, composition, and selectivity data taken over a 7 day period from a bench scale oligomerization reactor system.

Reactor Set-Up

The dehydration reaction of alcohols was carried out at 280-350° C. via a fixed bed reactor containing 2.5 g of specified catalyst, and flowing preheated (180° C.) vaporized alcohol in downward flow over the fixed catalyst bed. The flow rates of alcohols were controlled by Teledyne Model 500D syringe pumps coupled with D-Series pump controllers, and the alcohol flow rate was adjusted to obtain the targeted olefin WHSV (weight hourly space velocity). The reaction temperature was maintained constant via a Lindberg Blue M furnace as manufactured by Thermo-Scientific. Alcohol conversion was determined by analysis of condensed liquid phases of the reactor effluent by GC for residual alcohol content, and by weight of water phase collected in comparison to the theoretical amount of water expected for the overall reaction time and total amount of alcohol fed. Olefin isomeric distribution was determined by i) online gas analysis via SRI Instrument fitted with thermal conductivity detector and olefins calibrated relative to nitrogen flow across the reactor, and ii) sparging gaseous reactor effluent into chilled ethanol and injection on GC fitted with FID detector.

The oligomerization reaction of olefins was carried out at 110-280° C. by using a fixed bed reactor containing 2.9 g of specified catalyst, and flowing the liquefied olefins downward. The flow rates of hydrocarbons were controlled by Teledyne Model 500D syringe pumps coupled with D-Series pump controllers, and the olefin flow rate was adjusted to obtain the targeted olefin WHSV (weight hourly space velocity). The reaction temperature was maintained constant via a Lindberg Blue M furnace as manufactured by Thermo-Scientific. Olefin conversion was calculated by analysis of the liquid phase reactor effluent by GC for olefin content, and comparing mass accountability fed versus liquid mass collected. Catalyst screening required that mass accountabilities exceeded 90% for continued development and evaluation

EXAMPLES

Example 1a: Co-precipitated Zn/Zr-Zeolite H$^+$(Zeolyst CP-914C, Si/Al=20) Catalyst Preparation Zeolyst CP-914C (6 g) was calcined at 550 C for 4 hours to convert from ammonium cation to protonated H$^{30}$ form. The precursor metal salts (Sigma Aldrich) 2.84 g Zirconium (IV) oxynitrate hydrate and 0.57 g Zinc nitrate hexahydrate were added to deionized water (70 ml) resulting in a Zn/Zr metal molar ratio of 1/6.5. Upon salt dissolution, the salt solution was added to a 250 ml flask with magnetic stir bar and 6 g of Zeolyst CP-914C-H$^+$was added to the salt solution. The Zeolite was stirred for 10 minutes to assure complete wetting, and dropwise addition of 20% NaOH (4.5 g) was added to the slurry until pH=7.5. The resulting pH adjusted slurry was allowed to stir at room temperature for an additional 60 minutes. The slurry was filtered, washed with hot water (3×100 ml ), dried at 150° C. for 2 hrs and afterwards calcined at 500° C. for 4 hrs.

Example 1b: Nickel Impregnated $WO_x/ZrO_y$ Catalyst Preparation $WO_x/ZrO_y$+1.25% Ni catalyst was prepared by incipient wetness technique as described. Briefly, the precursor nickel salts (Sigma Aldrich) were added to deionized water in an amount to produce a nickel loading of 1.25 wt % upon addition to a known amount of $WO_x/ZrO_y$ catalyst (15% W) as support. The impregnated $WO_x/ZrO_y$ catalyst was dried at 140° C. for 4 h, and afterwards calcined at 550° C. for 4 h.

Example 2: Jet/Diesel formation

Oligomerization of mixed $C_4$-$C_8$ Olefin Feed derived from initial ethylene oligomerization (48% $C_4$'s, 36% $C_6$'s, 16% $C_8$'s, 0.8% $C_{10}$'s) over $WO_x/ZrO_y$+1.25% Ni. Reaction Conditions: 200° C., P=300 psig, WHSV=7.1, Recycle Ratio 3:1 (reactor effluent:mixed $C_4$-$C_8$ olefin feed), 98% mass accountability (Mass In/Mass Out), Isolated 67% Jet/Diesel Fraction post vacuum distillation. As per GC, the overhead 'lights' fraction representing 32% of the total oligomerization product mass was 16% $C_5$-$C_7$, 70% $C_8$, and 13% $C_9$-$C_{11}$ as a mixture of branched and linear olefins as per GC/MS.

Example 3: Jet/Diesel Formation

Oligomerization of mixed $C_4$ Olefin Feed (16.5% n-Butene, 16.5% cis_Butene, 16.5% trans-Butene, 50.5% Isobutylene) over $WO_x/ZrO_y$ +1.25% Ni. Reaction Conditions: 200° C., P=300 psig, WHSV=7.1, Recycle Ratio 6:1 (product:fresh butenes feed), >97% mass accountability (Mass In/Mass Out), Isolated 67% Jet/Diesel Fraction post vacuum distillation. As per GC, the overhead 'lights' frac tion representing 32% of the total oligomerization product mass was 16% $C_5$-$C_7$, 70% $C_8$, and 13% $C_9$-$C_{11}$ as a mixture of branched and linear olefins as per GC/MS.

Example 4: Jet formation

Oligomerization of mixed $C_4$ Olefin Feed (16.5% n-Butene, 16.5% cis-Butene, 16.5% trans-Butene, 50.5% isobutylene over un-doped Tungstated Zirconium (T=195° C., P=340 psig, WHSV=1.6). Single pass yields; Tabulated GC Area % of Oligomer Distribution

| % $C_4$ | % $C_5$-$C_7$ | % $C_8$ | % $C_9$-$C_{11}$ | % $C_{12}$ | % $C_{13}$-$C_{15}$ | % $C_{16}$ | % $C_{20}$ |
|---|---|---|---|---|---|---|---|
| 20.76 | 0.61 | 55.73 | 0.31 | 20.39 | 0.27 | 1.82 | 0.11 |

Mass Accountability=50%; Overall $C_4$ Olefin Conversion=51%
Area % C8 Fraction=54%; Area % $C_{12}$+Fraction=23%

Example 5: Diesel formation

Oligomerization of mixed $C_4$ Olefin Feed (16.5% n-Butene, 16.5% cis-Butene, 16.5% trans-Butene, 50.5% Isobutylene) over H+ZSM-5 (Type CBV-2314). Reaction Conditions: 280° C., WHSV=1.8, 95% Mass accountability (Mass In/Mass Out), Isolated 70% Diesel Fraction post vacuum distillation resulting in Cetane Value of >40.

Example 6: Diesel formation

Oligomerization of Propylene Feed over H+ZSM-5 (Type CBV-2314). Reaction Conditions: 280° C., WHSV=1.4, 95% Mass accountability (Mass In/Mass Out), Isolated 75% Diesel Fraction post vacuum distillation resulting in Cetane Value of >40.

Example 7: Diesel formation

Oligomerization of mixed linear butenes feed (33.3% n-Butene, 33.3% cis-Butene, 33.3% trans-Butene) over $WO_x/ZrO_y$+1.25% Ni+H+ZSM-5 (Type CBV-5524). Reaction Conditions: 230° C., WHSV=1.8, 95% Mass accountability (Mass In/Mass Out), Isolated 65% Diesel Fraction post vacuum distillation resulting in Cetane Value of >40.

Example 8: Jet Formation

Oligomerization of mixed linear butenes feed (33.3% n-Butene, 33.3% cis-Butene, 33.3% trans-Butene) over $WO_x/ZrO_y$+1.25% Ni+WZSM-5 (Type CBV-5524). Reaction Conditions: 180° C., WHSV=1.8, 95% Mass accountability (Mass In/Mass Out), Isolated 70% Jet Fraction post vacuum distillation.

Example 9: Jet Formation

Selective Oligomerization of mixed butenes feed (16.5% n-Butene, 16.5% cis-Butene, 16.5% trans-Butene, 50.5% Isobutylene) over $WO_x/ZrO_y$(15wt % W) Reaction Conditions: 110° C., WHSV=3.2, Table 1: 65% liquid mass accountability (mass in/mass out), 60% Jet selectivity ($C_{12}$+ oligomers); Table 2: 40% butenes unreacted consisting of ~90% linear $C_4$'s and ~10% isobutylene.

TABLE 1

| | Product Composition: Case i(mixed butenes only, 250 psig) | | | | | | | | |
|---|---|---|---|---|---|---|---|---|---|
| | % C4 | % C8 | % C12 | % C16 | % C20 | % C24 | Jet Selectivity | C4 Conversion | Mass Accountability |
| 0.21 ml/min, 110 deg C. | 13.3 | 29.4 | 40.8 | 11.8 | 1.9 | 0.3 | 56.2% | 57% | 66% |
| | 8.9 | 31.6 | 43.4 | 11.9 | 1.5 | 0.1 | 58.4% | 61% | 66% |
| | 10.8 | 31.6 | 42.4 | 11.3 | 1.4 | 0.1 | 56.6% | 60% | 67% |
| | 11.5 | 30.9 | 42.5 | 11.4 | 1.4 | 0.0 | 56.6% | 62% | 70% |

TABLE 2

| | Vented mass and composition: Case i (mixed butenes only, 250 psig) | | | |
|---|---|---|---|---|
| | total recoverable butenes (% of total initial butenes mass) | composition, recoverable butenes (mass %) | | |
| | | iC4 | linears | butanes |
| 0.21 ml/min, 110 deg C. | 43% | 10 | 88 | 1.3 |
| | 39% | 7 | 92 | 0.8 |
| | 40% | 7 | 92 | 0.7 |
| | 38% | 7 | 92 | 0.7 |

Example 10

Concurrent Dehydration/Isomerization of Fuel Grade Isobutanol over co-precipitated Zn/Zr-Zeolite-H+(Zeolyst CP-914C) Reaction Conditions: T=300° C., 2.5 g catalyst, WHSV=9.1, P=50 psig, >99% conversion of isobutanol, 75% linear butenes/25% isobutylene, trace amounts of organic phase containing $C_4$+ olefins.

Example 11

Dehydration of Fuel Grade Ethanol over co-precipitated Zn/Zr-Zeolite-H+(Zeolyst CBV-5524, Si/Al=50) Reaction Conditions: T=300° C., 2.5 g catalyst, WHSV=1.0, P=50 psig, >98% conversion of ethanol, >90% yield to ethylene with trace amounts or $C_3$ and $C_4$ olefins.

Example 12

Dehydration of a 75/25 wt % mixture of Fuel Grade Isobutanol and Fuel Grade Ethanol over co-precipitated Zn/Zr-Zeolite-H+(Zeolyst CBV-5524, Si/Al=50) Reaction Conditions: T=350° C., 2.5 g catalyst, WHSV=3.1, P=50 psig, >99% conversion of isobutanol and >90% conversion of ethanol. Vapor composition: 11% ethylene, 11% propylene, 45% isobutylene, 32% linear butenes.

Table 3: Oligomerization of mixed butylenes feed (3% n-Butene, 4% cis-Butene, 6% trans-Butene, 88% Isobutylene) over Tungstated Zirconium (T=130° C., P=225 psig, WHSV=6), Tungstated Zirconium (15% W), Recycle Ratio 6:1, Water level 1500 ppm, Alcohol level 6000 ppm.

TABLE 3

| Day | Beginning Recycle Jet Yield | Avg % Jet Yield in Reactor Effluent | C12/C16/C20 Ratio | % 244-C8 | % 234-C8 |
|---|---|---|---|---|---|
| 1 | 74.7 | 79.7 | 79.8/16.4/2.2 | 74.5 | 25.5 |
| 2 | 80.1 | 80.4 | 80.7/15.8/2.0 | 79.3 | 20.7 |
| 3 | 80.1 | 80.4 | 81.6/15.2/1.9 | 83.0 | 17.0 |
| 4 | 80.5 | 79.9 | 82.3/14.7/1.7 | 85.9 | 54.1 |
| 5 | 79.8 | 80.1 | 82.8/14.3/1.7 | 88.3 | 11.7 |
| 6 | 80.6 | 78.7 | 84.3/12.9/1.4 | 90.4 | 9.6 |
| 7 | 80.0 | 80.0 | 84.2/13.2/1.4 | 91.6 | 8.4 |

The following specific examples are intended to be illustrative of the invention and should not be construed as limiting the scope of the invention as defined by appended claims.

The foregoing detailed description has been given for clearness of understanding only and no unnecessary limitations should be understood there from as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The disclosures, including the claims, figures and/or drawings, of each and every patent, patent application, and publication cited herein are hereby incorporated herein by reference in their entireties.

What is claimed is:

1. A process for converting one or more $C_2$-$C_8$ linear or branched olefins to jet and/or diesel fuel, comprising contacting a feed stream comprising the one or more $C_2$-$C_8$ linear or branched olefins with a first catalyst and a second catalyst to afford a mixture comprising at least 70 wt % $C_{12}$ or greater alkenes, wherein the first catalyst comprises tungstted zirconium, molybdenum zirconium, or a combination thereof and the second catalyst comprises an acidic ZSM-5 catalyst.

2. The process of claim 1, wherein the one or more $C_2$-$C_8$ linear or branched olefins comprise at least about 50 wt % of butenes.

3. The process of claim 2, wherein the one or more $C_2$-$C_8$ linear or branched olefins comprise at least about 75 wt % of butenes.

4. The process of claim 3, wherein the one or more $C_2$-$C_8$ linear or branched olefins comprise at least about 90 wt % of butenes.

5. The process of claim 4, wherein said butenes comprises at least about 75 wt % isobutene.

6. The process of claim 4, wherein said butenes comprises at least about 75 wt % of linear butenes.

7. The process of claim 1, further comprising dehydrating one or more $C_2$-$C_8$ linear or branched alcohols with a third catalyst to provide the feed stream comprising one or more $C_2$-$C_8$ linear or branched olefins.

8. The process of claim 7, wherein said third catalyst comprises Zeolites, Group IB-VIIB metal doped zeolites) doped zeolites, or combinations thereof.

9. The process of claim 7, wherein said third catalyst comprises an acidic ZSM-5 catalyst.

10. The process of claim 9, wherein said acidic ZSM-5 further comprises from about 0.01 wt % to about 5 wt % zinc.

11. The process of claim 9, wherein said acidic ZSM-5 further comprises from about 0.01 wt % to about 20 wt % zirconium.

12. The process of claim 7, wherein said third catalyst comprises an acidic Ferrierite catalyst.

13. The process of claim 12, wherein said acidic Ferrierite further comprises from about 0.01 wt % to about 5 wt % zinc.

14. The process of claim 12, wherein said acidic Ferrierite further comprises from about 0.01 wt % to about 20 wt % zirconium.

15. The process of claim 7, wherein the feed stream comprising one or more $C_2$-$C_8$ linear or branched olefins comprises at least 0.5 wt % oxygenates.

16. The process of claim 15, wherein the feed stream comprising one or more $C_2$-$C_8$ linear or branched olefins comprises at least 1 wt % oxygenates.

17. The process of claim 16, wherein the feed stream comprising one or more $C_2$-$C_8$ linear or branched olefins comprises at least 2 wt % oxygenates.

18. The process of claim 17, wherein the feed stream comprising one or more $C_2$-$C_8$ linear or branched olefins comprises at least 3 wt % oxygenates.

19. The process of claim 15, wherein said oxygenates comprise water and one or more $C_2$-$C_8$ linear or branched alcohols.

20. The process of claim 1, wherein a single-pass converstion of said $C_2$-$C_8$ olefin is at least about 50%.

21. The process of claim 20, wherein the single-pass conversion of said $C_2$-$C_8$ olefin is at least about 60%.

22. The process of claim 21, wherein the single-pass conversion of said $C_2$-$C_8$ olefin is at least about 70%.

23. The process of claim 22, wherein the yield of said $C_{12}$ or greater alkenes is at least about 75%.

24. The process of claim 1, wherein said first catalyst comprises nickel and/or cobalt doped tungstated zirconium catalysts, nickel and/or cobalt doped molybdenum zirconium catalysts, or combinations thereof.

25. The process of claim 1, wherein said first catalyst is tungstated zirconium catalyst.

26. The process of claim 25, wherein said tungstated zirconium catalyst comprises about 85 wt % zirconium and about 15 wt % tungsten.

27. The process of claim 25, wherein said tungstated zirconium catalyst further comprises from about 0.01 to about 3 wt % of nickel.

28. The process of claim 25, wherein said tungstated zirconium catalyst further comprises from about 0.01 to about 3 wt % of cobalt.

29. The process of claim 1, wherein said first catalyst is nickel and/or cobalt doped molybdenum zirconium catalyst.

30. The process of claim 29, wherein said molybdenum zirconium catalyst comprises about 85 wt % zirconium and about 15 wt % molybdenum.

31. The process of claim 29, wherein said molybdenum zirconium catalyst further comprises from about 0.01 to about 3 wt % of nickel.

32. The process of claim 29, wherein said molybdenum zirconium catalyst further comprises from about 0.01 to about 3 wt % of cobalt.

33. The process of claim 1, wherein said first catalyst further comprises acidic Ferrierite, zeolites, Group IB-VIIB metal doped zeolites, doped zeolites, an acidic zeolite catalyst, or combinations thereof.

34. The process of claim 1, wherein said acidic ZSM-5 further comprises from about 0.01 wt % to about 5 wt % zinc.

35. The process of claim 1, wherein said acidic ZSM-5 further comprises from about 0.01 wt % to about 20 wt % zirconium.

36. The process of claim 1, wherein said first catalyst comprises an acidic Ferrierite catalyst.

37. The process of claim 36, wherein said acidic Ferrierite further comprises from about 0.01 wt % to about 5 wt % zinc.

38. The process of claim 31, wherein said acidic Ferrierite further comprises from about 0.01 wt % to about 20 wt % zirconium.

* * * * *